(12) United States Patent
Mann

(10) Patent No.: US 6,275,737 B1
(45) Date of Patent: *Aug. 14, 2001

(54) TRANSCUTANEOUS TRANSMISSION POUCH

(75) Inventor: Carla M. Mann, Beverly Hills, CA (US)

(73) Assignee: Advanced Bionics Corporation, Sylmar, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/338,701

(22) Filed: Jun. 23, 1999

Related U.S. Application Data

(63) Continuation-in-part of application No. 09/172,924, filed on Oct. 14, 1998, now Pat. No. 5,948,006.

(51) Int. Cl.⁷ .................................................. A61N 1/02
(52) U.S. Cl. .................................................. 607/61
(58) Field of Search .................. 607/32, 33, 60, 607/61; 128/903

(56) References Cited

U.S. PATENT DOCUMENTS

| | | | |
|---|---|---|---|
| 3,943,918 | 3/1976 | Lewis | 128/2.1 A |
| 5,314,453 | 5/1994 | Jeutter | 607/64 |
| 5,511,553 * | 4/1996 | Segalowitz | 128/903 |
| 5,578,065 | 11/1996 | Hattori et al. | 607/46 |
| 5,749,365 * | 5/1998 | Magill | 128/903 |
| 5,948,006 * | 9/1999 | Mann | 607/61 |

* cited by examiner

Primary Examiner—George R. Evanisko
(74) Attorney, Agent, or Firm—Bryant R. Gold

(57) ABSTRACT

A transcutaneous transmission pouch provides a pocket on a flexible substrate adherable to a user's skin. The flexible substrate is adhered to the user's skin closest to the location where an implantable device is implanted. An antenna coil, including associated electrical circuitry needed to transmit power and data signals to the implantable device from an external power/control source, are removably inserted into the pocket of the flexible substrate in order to hold the antenna coil in an aligned position with the implantable device during a power or data signal transfer.

6 Claims, 4 Drawing Sheets

US 6,275,737 B1

TRANSCUTANEOUS TRANSMISSION POUCH

This application is a continuation-in-part of application Ser. No. 09/172,924, filed Oct. 14, 1998 now U.S. Pat. No. 5,948,006.

BACKGROUND OF THE INVENTION

The present invention relates to the transfer of electromagnetic energy between a transmission coil and a receiver coil. More particularly, the invention relates to a pouch, secured to the skin of a patient, in which a transmission coil may be temporarily placed or held while electromagnetic energy is transferred to an implantable device through the transmission coil. Such electromagnetic energy transfer thereby allows for the transmission of power and/or data to the device and/or to a replenishable power source, e.g., a rechargeable battery, associated with the implantable device.

Various types of medical devices such as cochlear implants, neural muscular stimulators, implantable pumps, and other implantable devices have been developed that are designed to be surgically inserted within a patient's body to carry out a medically related function for an extended period of time. Although a lead connected to the implanted device and extending outside the patient's body can be used to supply electrical power required to energize the device and/or control data, any lead that passes through the skin increases the risk of infection if left in place for more than a few days.

As an alternative to having a lead or wire pass through the skin of the patient, power and/or data can be supplied to an implanted medical device via an RF or electromagnetic link that couples power from an external (non-implanted) coil to an internal (implanted) coil. So long as a suitable link, e.g., an inductive link, is established between these two coils, which means some sort of external power source must be carried by or worn by the patient, power and/or data can be continuously supplied to the implanted medical device from the worn or carried external device, thereby allowing the implanted medical device to perform its intended function.

It is also known to power an implanted medical device with a battery that is housed internal to the implanted device. However, any battery used for extended periods of time will eventually need to be either recharged or replaced. Replacing an internally implanted battery subjects the patient to further surgery and thus is not desirable, at least not on a frequent basis.

Rather than replace an implanted battery, the battery can be recharged by transcutaneously coupling power from an external source to an implanted receiver that is connected to the battery. Although power can be coupled from an external source at radio frequencies using matching antennas, it is generally more efficient to employ an external transmission coil and an internal receiving coil which are inductively (electromagnetically) coupled to each other to transfer power at lower frequencies. In this approach, the external transmission coil is energized with alternating current (AC), producing a varying magnetic flux that passes through the patient's skin and induces a corresponding AC voltage in the internal receiving coil. The voltage induced in the receiving coil may then be rectified and used to power the implanted device and/or to charge a battery or other charge storage device (e.g., an ultracapacitor), which in turn powers the implanted device. For example, U.S. Pat. No. 4,082,097 discloses a system for charging a rechargeable battery in an implanted human tissue stimulator by means on an external power source.

Some implantable devices, such as neural or auditory stimulators, do not require internal batteries as a power source, but rather receive power directly via a transcutaneous coupling. Still other implantable devices, in addition to receiving power directly from an external power source, may also transmit information and data back to an external device relating to the status of the device and the signals it senses in the patient's body. See, e.g., U.S. Pat. No. 5,603,726, which describes an implantable cochlear stimulator powered by an external wearable system; and U.S. Pat. Nos. 5,324,316; 5,312,439; and 5,358,514; which describe a small implantable microstimulator. All of these patents—the '726 patent, the '316 patent, the '439 patent, and the '514 patent—are incorporated herein by reference.

When electromagnetic coupling is used to transfer power and/or data to an implanted device, proper alignment of the external device and the implanted device is important for effective electromagnetic coupling. A common way of achieving the desired alignment between the external transmission coil and the implanted receiver coil is to employ a permanent magnet in both the headpiece which houses the external coil and the implanted device which houses the receiver coil. The magnetic attractive force associated with such magnets holds the external coil in close proximity to the receiver coil and provides the desired alignment between the coils so that inductive coupling may efficiently occur.

Another method of aligning an external unit with an implanted internal receiving device is shown in U.S. Pat. No. 5,545,191. In this patent, the external unit uses VEL-CRO® strips for attaching the external unit to the skin in a proper location for optimal electromagnetic coupling between the units.

As is known in the art, the efficiency with which electromagnetic power may be transcutaneously transferred between a transmission coil and a receiving coil, where one of the coils is implanted and the other is not, is a function of the alignment and distance between the coils. It is thus desirable to position the external device as close as possible to the implanted device.

Disadvantageously, existing external devices that supply electromagnetic power are bulky and large. These devices include a power source, control circuitry and transmission coil. The power source (e.g., a battery and control circuitry) is usually attached to a person's belt or pocket. The transmission coil must be placed on the skin at a location that is as close as possible to the implanted device. Such positioning has heretofore required some sort of alignment mechanism, e.g., permanent magnets in the implanted device and in an external head that carries the transmission coil. The use of such permanent magnets may not be desirable in all situations, and adds to the cost of the system. The transmission coil must also be attached to the power source and control circuitry via some sort of cable, which cable (depending upon how often the transmission coil must be used) may be a nuisance to the patient, and something that the patient considers obtrusive and unsightly.

In view of the above, it is evident that what is needed is a convenient way to easily align the external transmission coil, when used, with the implanted device, without the need to use permanent magnets. What is further needed is an unobtrusive external device that can transmit power and/or data transcutaneously to an implanted device, and wherein such external device is not only small and light weight, but is also readily attachable to the skin in close proximity to, i.e., substantially aligned with, the implanted device.

SUMMARY OF THE INVENTION

The present invention advantageously addresses the above and other needs by providing an external patch or pouch which is secured to the skin of its user above the location where an implantable device has been implanted. When an electromagnetic link needs to be established with the implantable device, a transmission coil, and related circuitry, is carried in, or may be temporarily inserted into a pocket formed in, the patch or pouch. Such positioning holds the transmission coil in alignment with the implanted device so that power and/or data can be efficiently transferred to the implanted device. The implanted device may comprise a tissue stimulator, e.g., a spinal cord stimulator (SCS), a sensor, pump or any other implantable device that requires an electromagnetic link to be established therewith. Typically, the electromagnetic link is used to power, or charge, a rechargeable power source, e.g., a rechargeable battery, included within the implanted device on an as-needed basis or in accordance with a prescribed recharging schedule, such as once a day, once every other day, once a week, or the like.

In one embodiment, a transcutaneous transmission patch is provided that is thin, light weight, and has an adhesive attached to one surface thereof to facilitate attachment of the patch to a patient's skin. That is, the patch includes a base having an adhesive backing (for attachment to the skin) and a closed pouch or cavity for housing the electronic components, e.g., a battery, a transmission coil, and electronic circuitry. Most or all of the electronic circuitry may be embodied in one or more integrated circuits.

The size of the transcutaneous transmission patch varies depending on the application with which the patch is used. Advantageously, it may be designed to receive any reasonably-sized battery, e.g., from a pair of AAA-sized batteries, to small disc-shaped watch/calculator/hearing-aid batteries.

The transcutaneous transmission patch is attached to a user's skin with an adhesive backing, similar to that used in a band-aid, or disposable transcutaneous electrical neuro stimulation (TENS) electrodes. In this way, the transcutaneous transmission patch can be removed and replaced, when required, with very little discomfort to the user.

Typically, the transcutaneous transmission patch is fully disposable. That is, when the transcutaneous transmission patch needs to be replaced, the old transcutaneous transmission patch is removed and discarded, and a new transcutaneous transmission patch is attached to the patient's skin.

In other embodiments, some of the components of a transcutaneous transmission patch (i.e., electronic circuitry, transmission coil, and/or batteries) may be removed and reused, while others of the components are discarded after use. In such instance, the pouch or cavity of the patch may be divided into at least two sections, separating the disposable and non-disposable components, thereby allowing easy removal of the non-disposable parts, as well as convenient discarding of the disposable parts.

In an additional embodiment of the invention, a transcutaneous transmission pouch is provided that is attached to a user's skin. The transmission pouch is thin, light weight, and has an adhesive attached to one surface thereof to facilitate its attachment to the patient's skin at the desired location. That is, the patch includes a base having an adhesive backing (for attachment to the skin) and has a pouch or cavity wherein a recharging head may be removably held. The recharging head includes an antenna coil through which power and/or data may be coupled to the implant device. In one embodiment, the recharging head includes within a single housing all of the electronic components, e.g, a battery, a transmission coil, and electronic circuitry, needed to transfer power to the implant device. In an alternative embodiment, the recharging head includes at least the antenna coil, and other circuitry needed to transfer power to the implant device through the antenna coil may be housed in a separate housing attached to the recharging head via a flexible cable.

In use, the transcutaneous transmission pouch is located as close as possible to the implanted device so as to provide the strongest signal coupling, and the recharging head is slid into or otherwise placed or held in the pouch. In one embodiment, circuitry included within or coupled to the recharging head responds to back telemetry or reflected or other signals from the implanted circuitry, to provide a visual and/or audible signal when the best coil alignment has been achieved.

It is thus a feature of the invention to provide a transcutaneous transmission pouch wherein a recharging head may be temporarily held that includes, or is electrically coupled to, all of the necessary circuitry, including a power source (when a power source is needed), needed to couple power and control signals into an implant device.

It is another feature of the invention, in accordance with one embodiment thereof, to provide such a transcutaneous transmission pouch that is fully disposable.

It is yet an additional feature of the invention to provide such a transmission pouch that readily attaches to the skin of a patient, using a suitable adhesive spread on one surface, much like disposable/reusable skin electrodes of the type commonly used with TENS units, thereby facilitating the pouch's positioning and adherence to the skin of a patient.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description of the presently contemplated best mode of practicing the invention is not to be taken in a limiting sense, but is made merely for the purpose of describing the general principles of the invention. The scope of the invention should be determined with reference to the claims.

Advantageously, a transcutaneous transmission system, used with a pouch or a patch, is compatible with many types of implanted devices, e.g., microstimulators, tissue stimulators, spinal cord stimulators, sensors, pumps, and the like. The transcutaneous transmission pouch or patch is self-adhering to the skin, easy to apply and remove, unobtrusive, can be made in variety of colors or shapes, is disposable and inexpensive. In one embodiment, alignment aids, e.g., an audible alarm (beeping sound) or visual signal (light emitting diode, or LED), or other perceivable signals, may be included as part of the circuitry intended for placement within the pouch, e.g., a recharging head, to signal when proper alignment with an implant device has been achieved.

One embodiment of the invention, described below in conjunction with FIGS. 7 and 8, relates to a transcutaneous transmission pouch that provides a convenient way to hold an external transmission coil (e.g, as part of a recharging head) so that it will be in proper alignment with an implanted receiving coil of an implant device, thereby allowing power and/or data signals to be sent to the implant device. Typically, such transmission is done for the purpose of recharging a replenishable power source, e.g., a rechargeable battery, that is included as part of the implant device. Such recharging is usually done in accordance with a periodic schedule, e.g., once or twice a day, once every other day, once a week, or the like.

Another embodiment of the invention relates to a transcutaneous transmission patch, described below in conjunction with FIGS. 2–5, wherein at least some of the electronic components and circuitry needed for powering an implant device are permanently or removably carried within a pouch, pocket or cavity of a patch that includes an adhesive surface adapted to stick or adhere to the skin.

Figure 1:
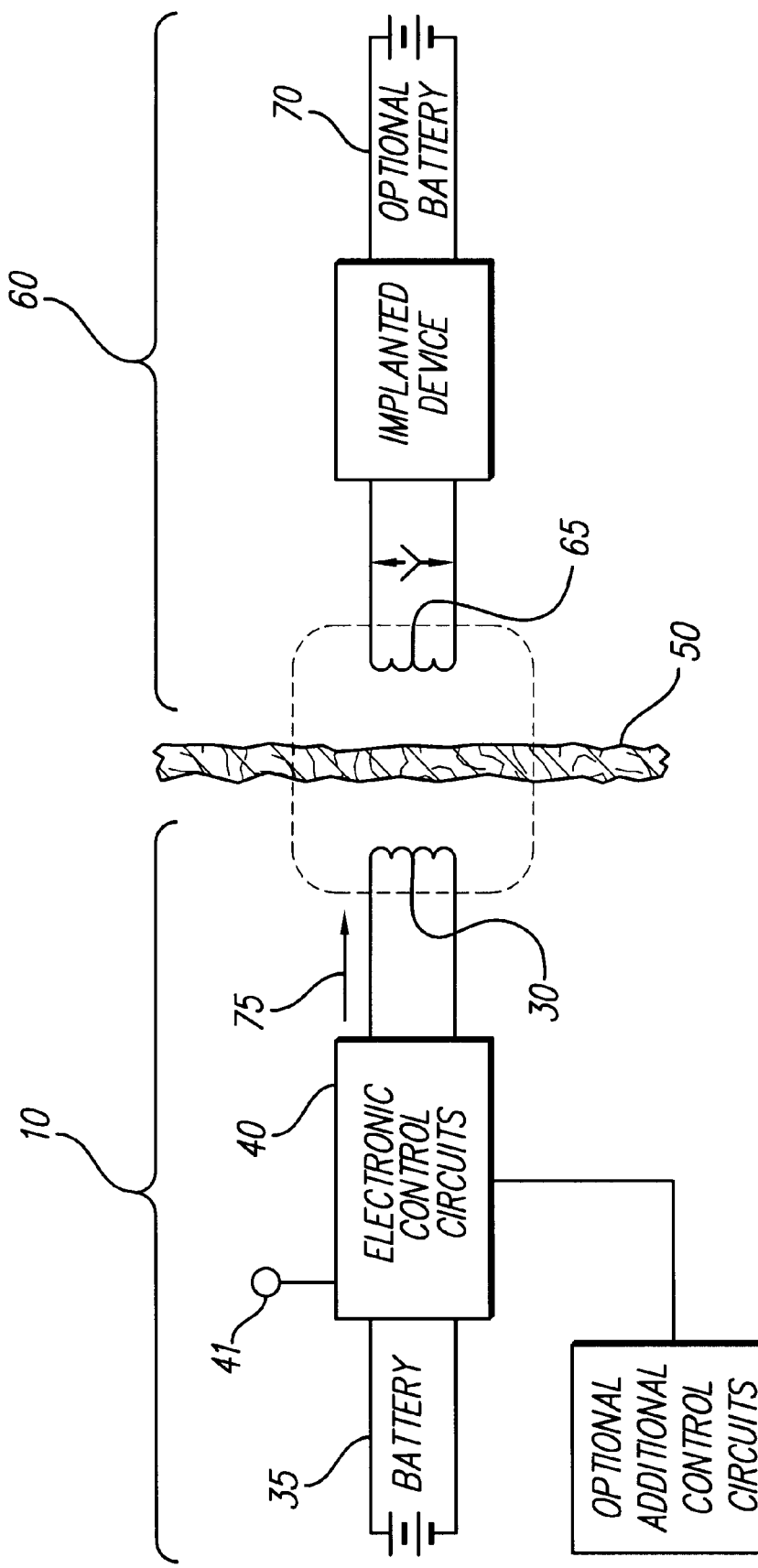
FIG. 1 is a block/schematic view of a transcutaneous transmission system in accordance with the present invention.

Before describing these two main embodiments of the invention, it will first be helpful to understand the manner in which a transcutaneous transmission system operates, i.e., how power is transmitted from an external (non-implanted) power source to an implanted device. To that end, reference is made to FIG. 1, where a transcutaneous transmission system is shown. As seen in FIG. 1, such system includes an external portion 10 used with an implantable device 60 (such as an implanted neural stimulator or microstimulator or sensor). The external portion 10 of the system includes electronic components and circuitry that transmits a modulated signal 75 from an external transmission coil 30, through the skin layer 50, to an internal receiving coil 65 of the implanted device 60. The modulated signal 75 is controlled by electronic control circuits 40 powered by a battery 35, or other power source (e.g., a super capacitor, ultracapacitor, or other energy-storage device). Circuitry within the implanted device 60 demodulates the signal to obtain data, and/or rectifies the signal to obtain power, as is known in the art. The recovered data may be used to control the operation of the implanted device 60. Optionally, the implanted device 60 may also contain a battery 70 or other power source, e.g., an ultracapacitor. The battery or other power source 70 is preferably of the rechargeable type, in which case, the external circuitry 10 is used to supply the power for recharging the battery 70 or other power source with power derived from the modulated signal 75. Hence, the external portion 10, without the need for any through-the-skin connectors, and without the need for any complex implanted multiplexing schemes or circuitry, is able to selectively control and/or power the implanted stimulator 60.

In some embodiments, the implanted device 60 may include back telemetry circuitry that allows the transmission of data and signals to be sent from the implanted system 60 to the external device 10. Such back telemetry data may include, e.g., an indication of the voltage level obtained by rectifying and filtering the inductively-coupled carrier signal received from the external portion 10. Such voltage will be at a peak (maximum) value when the implant coil 65 and external coil 30 are properly aligned. Thus, such signal may be used as a feedback signal to trigger circuitry within the external portion whenever proper alignment and/or improper alignment exists. The external portion, in such embodiments, may include a suitable audible and/or visual indicator 41 that alerts the patient (or other person who is positioning the external portion 10 on the skin of the patient) when proper coil alignment has been achieved.

It should be noted that other types of feedback signals could also be used to provide the needed alignment information for such optional alignment-indicating circuitry, all of which could be used with the invention. For example, circuitry within the external portion 10 may monitor, on a sampled basis, the reflected impedance as seen by the coil 30. Such impedance, depending upon how it is monitored, will reach either a maximum or a minimum when proper alignment is achieved. Still by way of example, circuitry within the external circuitry 10 could acoustically monitor reflected signals from devices implanted near the skin in order to locate such devices, much like a stud finder finds studs behind a wall.

Figure 2:
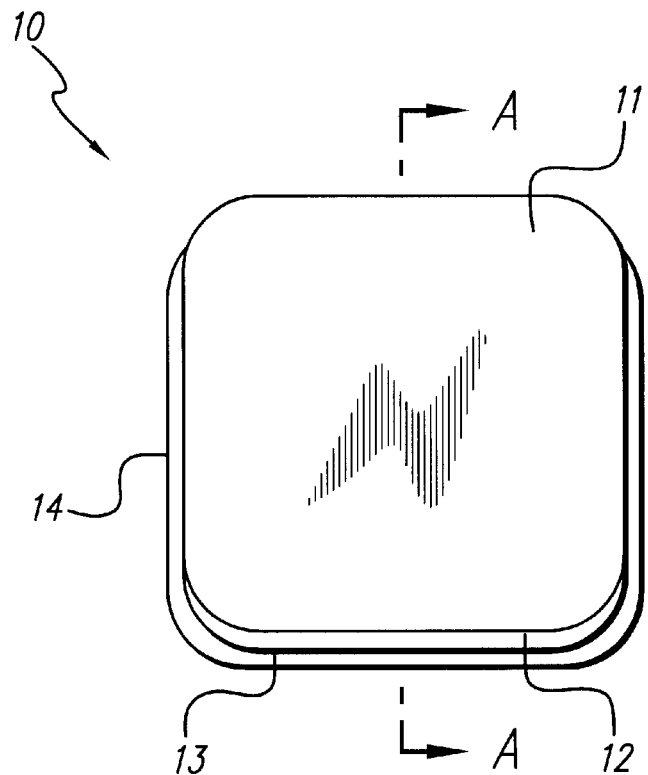
FIG. 2 is a top view of a transcutaneous transmission patch.

FIG. 2 illustrates one embodiment of the invention wherein the external portion 10 is carried within a transcutaneous transmission patch, a top view of which is shown in FIG. 2. In accordance with the embodiment of FIG. 2, the electronic circuitry and other components of the external system 10, e.g., batteries, integrated circuits, receiver coil, and the like, are embedded or otherwise carried in or on a flexible material 12 having a top surface 11 and an adhesive base 13, upon a removable backing 14. (Note, hereinafter, with reference to the description that follows in connection with FIGS. 2–6, the external portion 10 of the system may also be referred to as the "external patch 10", or just the "patch 10", inasmuch as it is within the patch that the external portion 10 of the system is carried or placed.) The patch 10 may be readily adhered to the skin of the patient by simply removing the backing 14, e.g., by peeling the backing away from the adhesive base 13, and then positioning the patch on the skin at the desired location. As explained above, the transmission patch 10 is used to supply power and/or data to an implanted device 60, such as a stimulator, pump or other device that requires power and/or data to be coupled thereto transcutaneously.

Figure 3:
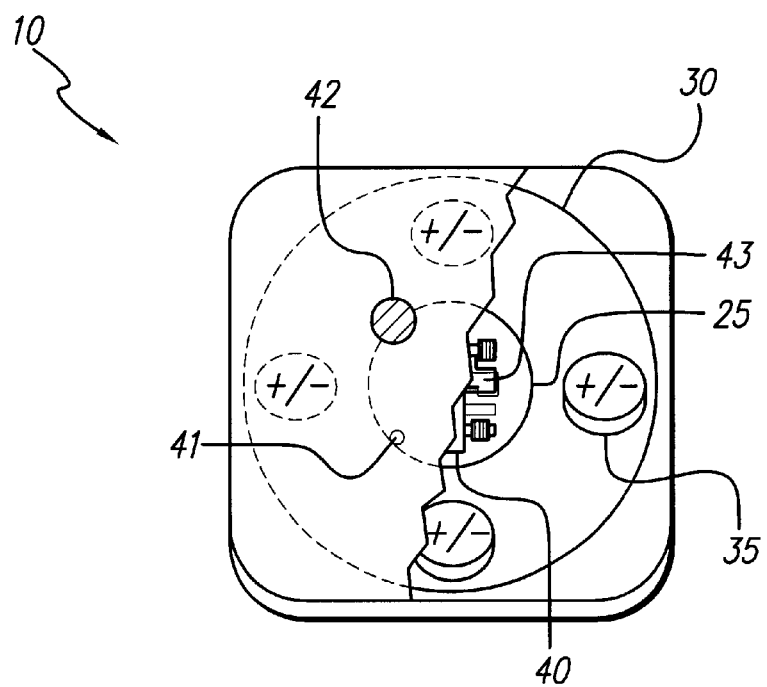
FIG. 3 is a top view similar to FIG. 2 with the top layer partially removed to show more detail of the interior components of one embodiment.

FIG. 3 similarly shows a top view of the transmission patch 10, but with part of the top surface peeled back to show some detail associated with the interior components. Such components include, e.g., a set of batteries 35, an electronic substrate 25 with integrated circuit (IC) chip 40 and other electronic componentry 43, and a transmission coil 30. FIG. 3 also shows optional surface components including a visual alignment indicator 41 (such as an LED or light) and an on/off switch 42 (such as a depressable button). Because the costs associated with the manufacture of IC chips and coils have reduced in recent years, one embodiment of the invention contemplates that the entire transcutaneous transmission patch 10 may be disposable. Alternatively, all or part of the transcutaneous transmission patch 10 may be reused, as will be discussed later.

Figure 4:
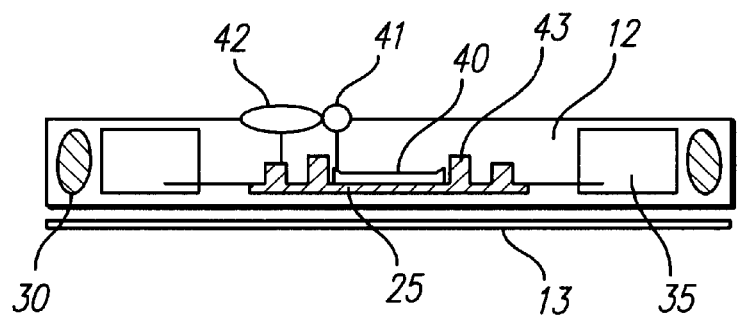
FIG. 4 is a cross-sectional view taken along the line A—A of FIG. 2 showing the transmission patch in use with an implanted stimulator.
Figure 5:
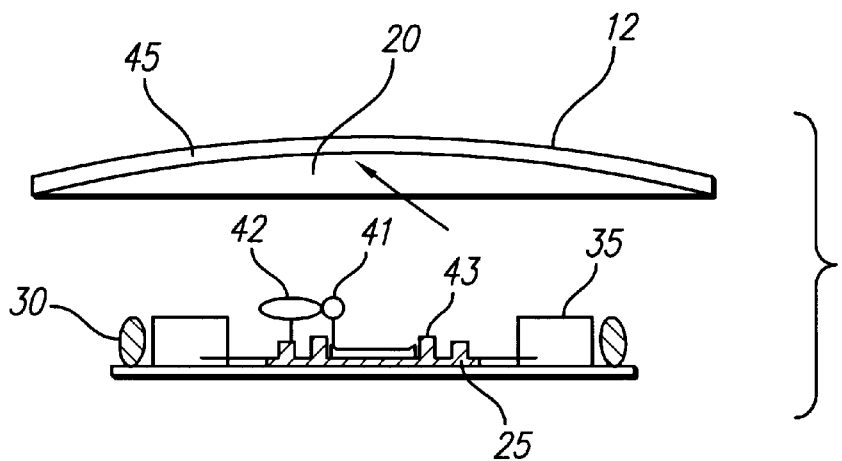
FIG. 5 is a cross-sectional view taken along A—A of FIG. 2 showing an alternate embodiment of the transmission patch in use with an implanted stimulator.
Figure 6:
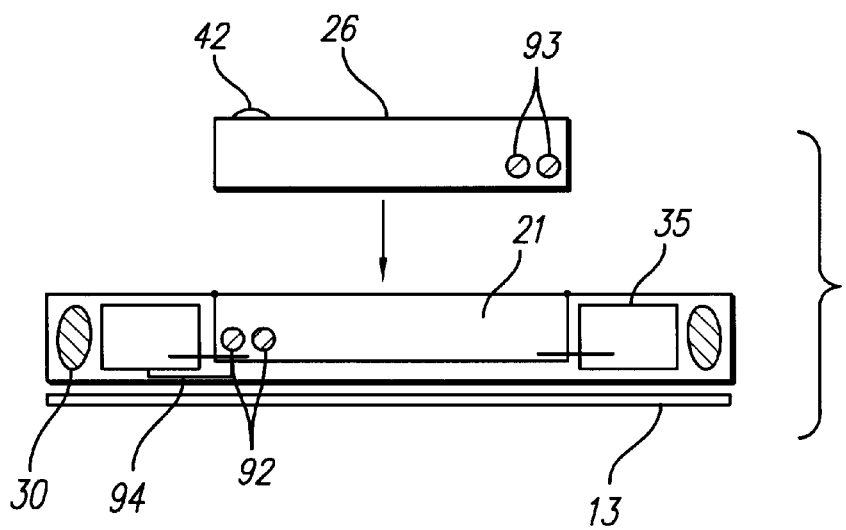
FIG. 6 is a cross-sectional view taken along A—A of FIG. 2 of yet another embodiment of the transmission patch, illustrating the manner in which a button-module, containing, e.g., electrical circuitry, may be detachably snapped into a cavity located within a flexible substrate, the flexible substrate having a coil and batteries embedded therein.

FIGS. 4–6 illustrate cross sectional views of 3 embodiments of the patch 10 taken along the line A—A of FIG. 2. FIG. 4 illustrates a fully disposable embodiment. As seen in FIG. 4, all of the electronic circuitry is embedded in a flexible base material 12 (hereafter referred to as the patch base material). The electronic circuitry includes a substrate 25 supporting Integrated Circuit (IC) chip 40 and other electronic components 43, a transmission coil 30, and batteries (or other power units) 35. In some embodiments of the invention, an alignment indicator 41 may be mounted on the IC chip 40 to provide a signal that indicates when proper coil alignment has been achieved. Likewise, in some embodiments of the invention, an on/off switch 42 may be added into the circuitry so that a single patch can be intermittently used, before being discarded. In a fully disposable embodiment, once the batteries (or other power units) 35 in the transcutaneous transmission patch 10 are discharged, the patch 10 is removed and a new transcutaneous transmission patch 10 is applied.

Although the batteries illustrated in FIG. 3 are shown as being button shaped batteries of the type commonly used in watches, calculators, and hearing aids, it is to be understood that other types or shapes of batteries may also be employed, e.g., cylindrical AAA type batteries. It is also to be understood that other types of power storage devices, e.g., an ultracapacitor(s), may also be used within the patch 10 and/or the implant device 60, to provide needed operating power. Ultracapacitors (which are also commonly referred to as supercapacitors), as is known in the art, have a very high energy density, which means they are able to store large amounts of energy in a small volume or space. Unlike batteries, which produce energy electrochemically, a capacitor only stores energy that it receives from an external source. Nevertheless, once charged (i.e., once an ultracapacitor has energy stored therein from an external source), an ultracapacitor may provide a very usable power source, which can be readily recharged, as frequently as required, in which case it would be advantageous to include the reusable power source within a removable substrate.

In one embodiment, illustrated in FIG. 5, the compartment 20 of the transmission patch 10 comprises a pouch having an opening 45, e.g., along one edge thereof, allowing access for the insertion of components. The contents of the pouch 20 (substrate 25 with the transmission coil 30, batteries 35 and IC chip 40) are inserted through the opening 45. Such opening 45 may be sealed (closed) or unsealed (open) using a zip-lock or adhesive mechanism as is known in the art. In another embodiment, certain components could be left off of the removable substrate 25, and would be embedded within the patch 10 to be part of the disposable component group, e.g. transmission coil 30 and/or batteries (or other power units) 35. Thus, in FIG. 5, there is a disposable portion including at least the patch itself, and a re-usable portion that contains some or all of the electronic components for transmitting power and/or data to the implanted device 60.

In another embodiment, the compartment 20 of the transcutaneous transmission patch 10 comprises a cavity having an opening at its top into which the components of the transmission patch may be detachably inserted, e.g., snapped into position within the cavity, as shown in FIG. 6, discussed in more detail below. It may be advantageous to encase the reusable electronic circuitry, e.g. IC 40, into a button module 26 hat can be snapped into the cavity 21 formed in the patch base 12.

For embodiments of the invention which reuse some of the components (as opposed to disposing of the entire patch, including all of its components), many different combinations of reusable verses disposable components are envisioned. For example, just the batteries 35 may be reused (snapped into cavity 21) with chip 40 and other components embedded in the patch 10. Alternatively, the transmission coil 30 and IC chip 40 may be reused, and the patch substrate 25 and batteries 35 may be disposed. Still further, the patch base material 12 may have a transmission coil 30 embedded therein, and the patch base/coil may be disposable. One or more batteries 35 may also be housed on substrate 25 to be selectively removable and disposable therefrom, separately from the disposable patch. Thus, the patch may be disposed of with daily usage, while the battery may be used for weeks with the removable substrate and replaced after depletion. Thus, it is seen that a wide variety of combinations of disposable and reusable components may be used with the invention. In this way, the patient can reuse the more expensive items (e.g. electronics substrate 25 with batteries 35) and replace the inexpensive items (e.g. patch with coil 30). Such alternative design options are all within the scope of this invention and are guided by cost and usage requirements.

Referring again to FIG. 4, it is seen that the transcutaneous transmission patch 10 is designed to be secured to the skin of a patient 50. The patch 10 includes an adhesive base 13. Preferably, the patch 10 is constructed of flexible nonrigid materials in order to conform to the contour of the portion of the user's skin 50 to which the patch 10 is attached and can be made in a variety of shapes and colors (like skin color or designer colors). The adhesive base 13 is similar in construction to a band aid or TENS electrode, using a breathable, conformable, elastic adhesive bandaging material as is known in the art With reference to the embodiment shown in FIG. 6, the cavity 21 includes a plurality of coil terminals 92 formed in a side wall thereof. Such terminals are electrically connected, through wires 94 that pass through the patch base material 12, to the embedded coil 30, and/or other disposable circuit components. The coil 30 typically comprises multiple turns of suitable-sized fine wire.

The button module 26, which is adapted to snap into the cavity 21, includes suitable electrical contact points 93 along one of its edges. These contact points are electrically connected to the electrical/electronic circuitry 43 included within the module 26. When the module 26 is snapped into the cavity 21, a lip or ridge around the periphery of the cavity 21 may be used to help seal the interface between the removable module 26 and cavity 21. Further, when the module 26 is snapped into the cavity 21, the electrical contact points 93 are oriented so as to make electrical contact with the terminals 92 of the patch base material 12. As needed, the module 26 may be physically keyed to assure that the desired electrical contact is established. Alternatively, the contact points 93 may comprise annular rings, and the terminals 92 in the wall of the cavity 21 may be vertically spaced apart, so that regardless of the orientation of the module 26 as it is snapped into the cavity 21, the desired electrical connection is made, thereby electrically connecting the coil 30 and/or other embedded components to the electrical circuits within the module 26.

As indicated previously, some embodiments of the invention include an indicator 41 that provides a visual and/or audible indication when the proper alignment has been achieved with the implanted receiving coil. For such embodiments, the user of the device may leave the removable backing 13 in place while sliding (or otherwise moving and repositioning) the patch over the skin in order to find the proper location for affixing the patch. Once such location is found, then the removable backing 14 may be peeled away, and the patch 10 may be readily adhered to the found location.

It is contemplated that for some embodiments of the invention, the electronic circuitry 43 will include selective switch means for selectively enabling the visual/audible indicator 41. For example, a magnetically activated switch may be included in such circuitry so that when a small permanent magnet is placed over the area of the patch 10 under which the electronic circuitry 43 is located, the switch is activated to enable the visual/audible indicator 41. Once the patch has been affixed to the skin, such magnet can be removed, disabling the visual/audible indicator 41, thereby conserving power. Other types of enabling/disabling switches could, of course, also be used for this purpose, or other purposes.

For embodiments that do not include a user on/off switch (e.g. a depressable button or touch/heat sensitive surface) some means for turning the power on when a patch is being used is preferred so that stored transmission patches containing individual power sources would not be depleted before use. Hence, a patch 10 may include means for automatic activation as soon as the peel back surface 14 is removed from the adhesive 13. Likewise, the patch could be activated only when alignment with the implant is detected, a magnetic interface with the implant is detected, or proximity to the skin of the user is detected through a built-in temperature sensor. Thus, it is seen that any means for automatically or selectively activating a power source as is known in the art would be within the scope of the invention for turning the patch on or off.

In embodiments where the transmission patch is used not only for powering or recharging the implant, but also for controlling the operation of the implant, stored control information is required in the electronic circuitry of the patch for individual patients. Thus the transmission patch would also be programmable. The patches could be pre-programmed with stored information, or the patient may have a patch programmer that stores information for that patient to download software control information to each patch before use. For example, a neural stimulator may have many parameters for stimulating that are programmable for a patient including pulse width, frequency, and amplitude. The patient may use a patch programmer, that stores the patient's selected values for those and other parameters, to set the control output of the patch. Likewise, the patient could use the programmer to vary patch settings as needed. This approach would also be valuable in setting patch outputs for controlling the operation of implantable pumps and sensors.

Figure 7:
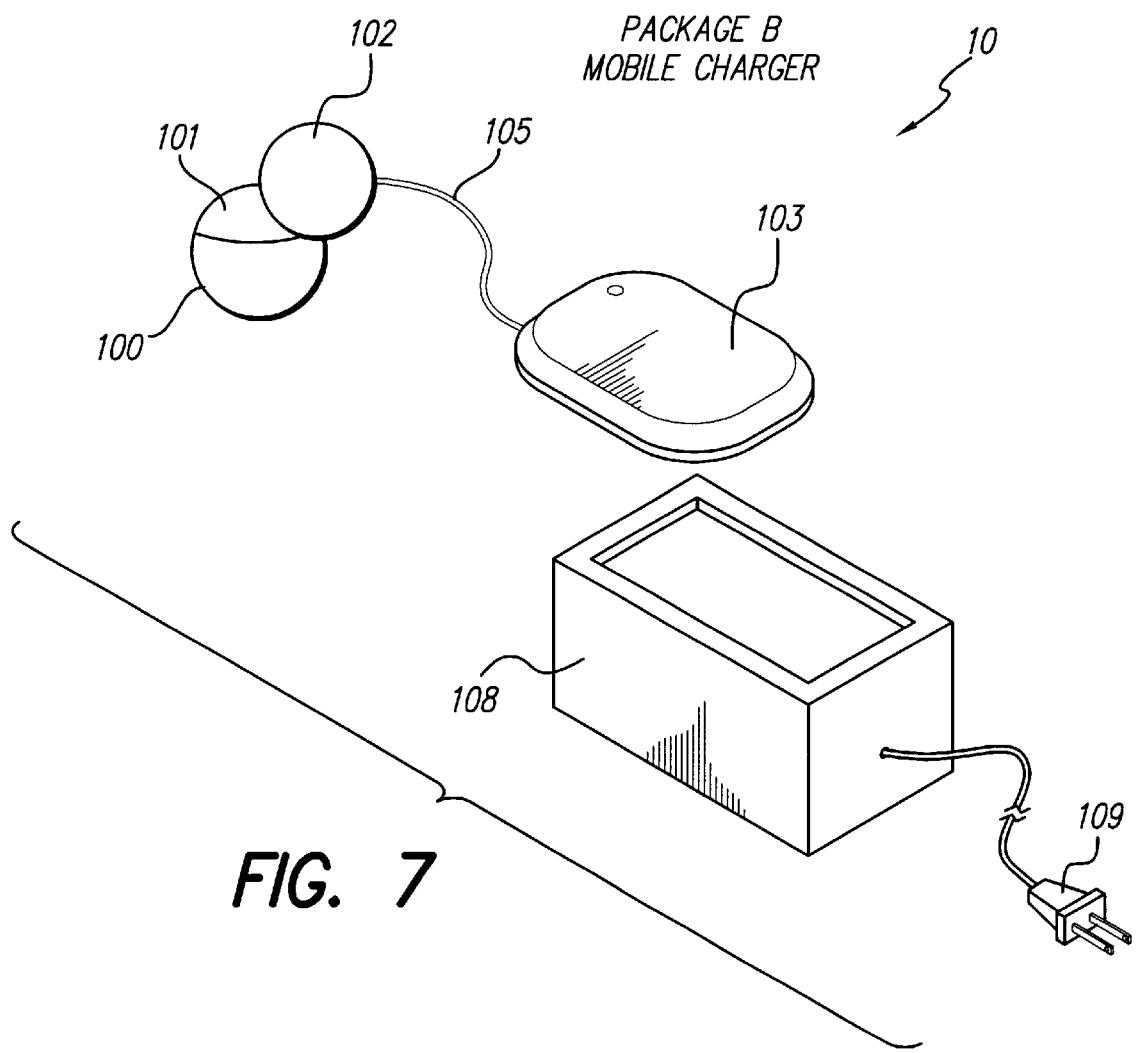
FIG. 7 illustrates one embodiment of a disposable transmission pouch used to hold or secure a recharging head of one type of a mobile charger unit.
Figure 8:
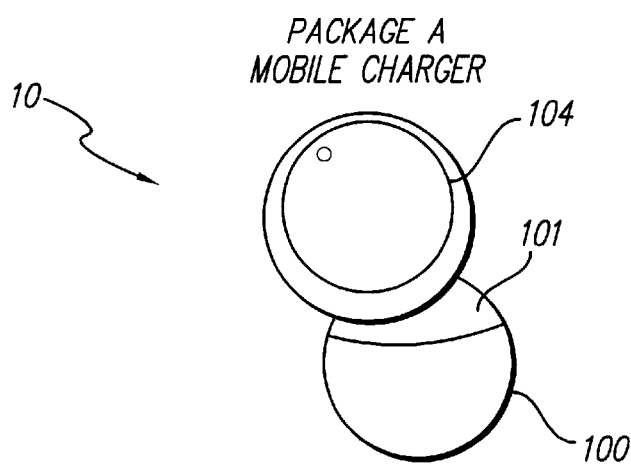
FIG. 8 illustrates a transmission pouch used to hold or secure a self-contained recharging unit in accordance with the invention.

Yet another embodiment of the invention is depicted in FIGS. 7 and 8. In these figures, a transcutaneous transmission pouch 100 is provided in which the external portion 10 (FIG. 1) of the system may be removably carried. When such pouch 100 is used, the external circuitry and other electrical components, e.g., an antenna coil, are typically housed within a charging head 102. For the embodiment shown in FIG. 7, the charging head 102 is attached to a charging unit 103 by way of a flexible cable 105. The charging unit 103 contains additional electronic circuitry, including a rechargeable battery (or other replenishable power source), which may be removably inserted into a charging port 108, or charging cradle 108.

In use, when the charging unit 103 is not in use, it may be stored in the charging port 108, where it becomes charged by way of electrical energy received through a conventional power cord 109 and conventional charging circuitry within the unit 103. Once fully charged, the charging unit 103, with charging head 102 attached thereto, becomes a mobile charging system that may be taken to wherever the patient is located. The charging head 102 may then be slipped inside of a pocket 101 formed within the pouch 100. The pouch 100 is includes an adhesive backing that allows it to be attached to the skin of the patient at a location on the patient's skin that is proximate the implanted device. Hence, when the charging head 102 is slipped into the pocket 101 of the transmission pouch 100, it is aligned with the implanted device, and power and/or data may be efficiently transmitted from the unit 103, through the charging head 102 to the implanted device.

FIG. 8 illustrates a different type of mobile charger unit 104 that may be used with the invention. As seen in FIG. 8, the mobile charger unit 104 comprises a round, disk-shaped housing wherein electrical components and other circuitry needed to send power and/or data signals to the implanted device are housed. Such charger unit 104 is thus totally self-contained, and does not need to be connected to any other units by way of a cable, or other connection, in order to perform its function of sending power and/or data signals to the implanted device. Thus, in use, the charger unit 104 is inserted inside of the pocket 101 of the transmission pouch 100, and when so inserted, is aligned with the implanted device so that power and/or data signals can be efficiently transmitted thereto. In one embodiment, the disk-shaped charger unit 104 may have removable batteries therein that are replaced, when needed. In another embodiment, the charger unit 104 may have rechargeable batteries (or any other replenishable power source) therein, which power source may be recharged, when needed, by coupling the unit 104 to a suitable replenishing unit, e.g., a suitable cradle 108 similar to the shown in FIG. 7. Alternatively, such connection may be made through a cable connection that plugs into the unit 104, that is inductively coupled to the unit 104, or that is electrically or electromagnetically or optically coupled through other means.

The transmission pouch 100 shown in FIGS. 7 and 8, including its adhesive backing, may be made of the same materials and in the same manner as is the transmission patch 10 described in connection with FIGS. 2–6.

From the above, it is thus seen that the present invention provides an unobtrusive way for the external portion of a powering/control system to be carried and positioned by a patient on the patient's skin so that power and/or data signals can be efficiently coupled into an implantable device. That is, it is seen that the invention allows the external portion to be carried in a pocket of a transmission pouch; or allows the external portion to be embedded, and/or partially carried, in a transcutaneous transmission patch. Regardless of whether the transmission pouch, or the transmission patch, is used, both are advantageously self-adhering to the skin, easy to apply and remove, unobtrusive, made in variety of colors or shapes, disposable and inexpensive. Moreover, some or all of the components of the tanscutaneous transmission patch may be recycled and reused, as desired.

While the invention herein disclosed has been described by means of specific embodiments and applications thereof, numerous modifications and variations could be made thereto by those skilled in the art without departing from the scope of the invention set forth in the claims.

What is claimed is:

1. A method for transmitting signals through the skin of a user to a receiving coil of an implantable unit, comprising the steps of:
   (a) providing a flexible transcutaneous pouch having a pocket formed therein wherein electronic circuitry coupled to a power source for transmitting signals to the implantable unit may be removably carried, the transcutaneous pouch having means for adhesively securing the transcutaneous pouch to a surface of the user's skin; and
   (b) detachably securing the transcutaneous pouch to the user's skin at a position that allows signals to be coupled from the electronic circuitry to the implantable unit; and
   (c) inserting the electronic circuitry into the pocket of the transcutaneous pouch; and
   (d) coupling the power source to the electronic circuitry carried in the pocket of the transcutaneous pouch, wherein the electronic circuitry is enabled and transmits signals to the implanted unit.

2. The method of claim 1 wherein step (c) comprises inserting the electronic circuitry and power source into the pocket of the transcutaneous pouch.

3. A transcutaneous transmission pouch assembly, comprising a transcutaneous transmission system, wherein the transcutaneous transmission system includes an implantable portion and an external portion, and wherein the external portion includes a first antenna coil and electrical circuitry means for transmitting at least one of power and data signals through the first antenna coil for coupling to the implantable portion; and a transcutaneous transmission pouch comprising:
   a flexible substrate adherable to a users skin; and
   a pocket formed in the flexible substrate;
   wherein the first antenna coil and at least a first portion of the electrical circuitry means, when placed in the pocket of the flexible substrate, are sufficiently aligned with the implantable portion of the transcutaneous transmission system to allow at least one of the power and data signals to be efficiently coupled into the implantable portion.

4. The transcutaneous transmission pouch assembly as set forth in claim 3 wherein the flexible substrate includes an adhesive base and a removable backing covering the adhesive base.

5. The transcutaneous transmission pouch assembly as set forth in claim 4 wherein the external portion includes a housing, and wherein the first antenna coil and the first portion of the electrical circuitry means associated with the non-implantable portion are carried within the housing, and further wherein the housing fits within the pocket of the flexible substrate.

6. The transcutaneous transmission pouch assembly as set forth in claim 4 wherein the external portion includes a housing, and wherein the first antenna coil and all of the electrical circuitry means associated with the external portion are carried within the housing, and further wherein the housing fits within the pocket of the flexible substrate.

* * * * *